US 6,459,937 B1
Oct. 1, 2002

(54) ENDOCARDIAL PACING LEAD WITH DETACHABLE TIP ELECTRODE ASSEMBLY

(75) Inventors: Kevin L. Morgan; Gene A. Bornzin, both of Simi Valley; Anne M. Pianca, Valencia, all of CA (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 09/558,484

(22) Filed: Apr. 25, 2000

(51) Int. Cl.$^7$ .................................................. A61N 1/05
(52) U.S. Cl. ...................................... 607/126; 607/119
(58) Field of Search ............................... 607/119, 126, 607/127, 128, 129, 122

(56) References Cited

U.S. PATENT DOCUMENTS

| | | | | |
|---|---|---|---|---|
| RE30,366 E | * | 8/1980 | Rasor ........................... 607/36 |
| 4,258,724 A | | 3/1981 | Balat et al. ................. 128/785 |
| 4,506,680 A | * | 3/1985 | Stokes .......................... 607/120 |
| 4,538,623 A | * | 9/1985 | Proctor ......................... 607/122 |
| 4,679,572 A | * | 7/1987 | Baker, Jr. ..................... 607/127 |
| 5,179,962 A | | 1/1993 | Dutcher et al. .............. 128/785 |
| 5,456,707 A | * | 10/1995 | Giele ........................... 607/127 |
| 5,755,762 A | * | 5/1998 | Bush ........................... 607/122 |
| 5,807,399 A | | 9/1998 | Laske et al. ................. 607/126 |

* cited by examiner

*Primary Examiner*—George R. Evanisko
*Assistant Examiner*—R. Bradford

(57) ABSTRACT

A body implantable lead assembly includes a lead body and a tip electrode assembly at the distal end of the lead body. The tip electrode assembly is detachably connected to the lead body by means of a threaded coupling actuatable by a stylet inserted through the lumen of the lead body. The lead body may therefore be removed leaving behind a chronically implanted tip electrode assembly. The invention has particular utility in the context of passive endocardial heart pacing leads whose tip electrode assemblies include tines which become entangled in the trabecular network of the heart, and are therefore difficult to remove.

8 Claims, 3 Drawing Sheets

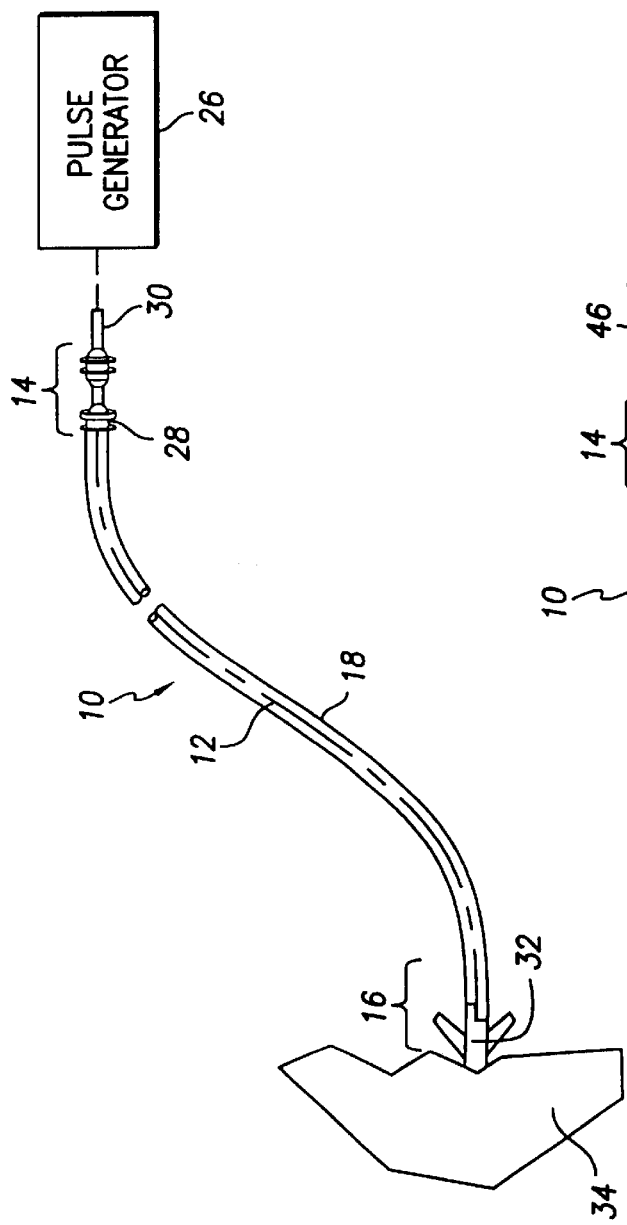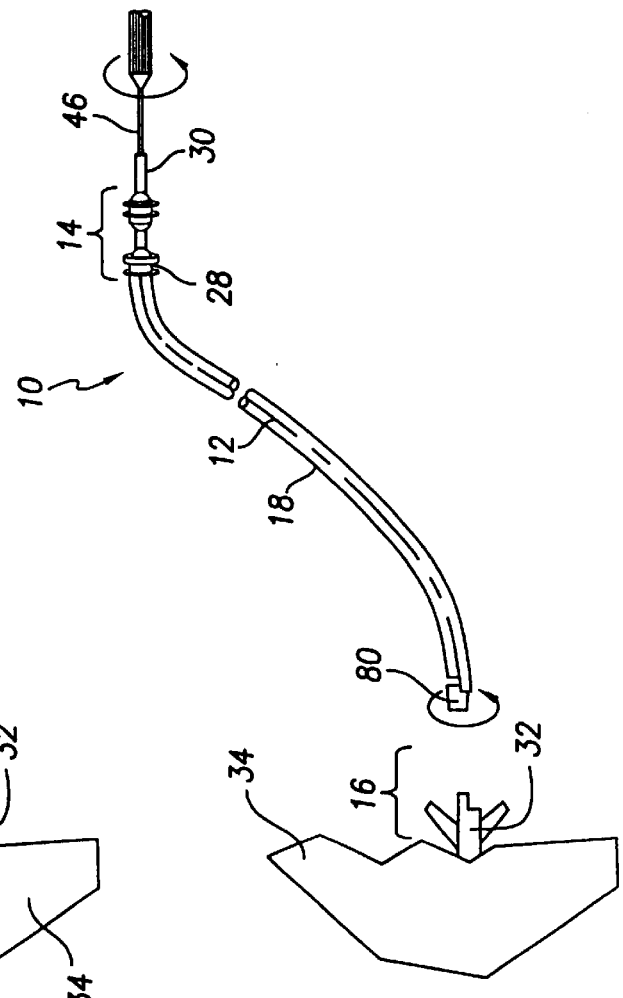

ENDOCARDIAL PACING LEAD WITH DETACHABLE TIP ELECTRODE ASSEMBLY

FIELD OF THE INVENTION

The present invention relates generally to implantable medical devices for providing stimulating pulses to selected body tissue, and more particularly, to the lead assemblies connecting such devices with the tissue to be stimulated.

BACKGROUND OF THE INVENTION

Although it will become evident to those skilled in the art that the present invention is applicable to a variety of implantable medical devices utilizing pulse generators to stimulate selected body tissue, the invention and its background will be described principally in the context of a specific example of such devices, namely, cardiac pacemakers for providing precisely controlled electrical stimulation pulses to the heart. However, the appended claims are not intended to be limited to any specific example or embodiment described herein.

Pacemaker leads form the electrical connection between the cardiac pacemaker pulse generator and the heart tissue which is to be stimulated. As is well known, the leads connecting such pacemakers with the heart may be used for pacing, or for sensing electrical signals produced by the heart and representing cardiac activity, or for both pacing and sensing in which case a single lead serves as a bidirectional pulse transmission link between the pacemaker and the heart. An endocardial type lead, that is, a lead which is inserted into a vein and guided therethrough into a cavity of the heart, includes at its distal end a tip electrode having an active tip surface designed to intimately contact the endocardium, the tissue lining the inside of the heart. The lead further includes a proximal end having a connector pin adapted to be received by a mating socket in the pacemaker. A flexible, coiled conductor surrounded by an insulating tube or sheath couples the connector pin at the proximal end and the electrode at the distal end.

To prevent displacement or dislodgment of the tip electrode and to maintain the necessary stable electrical contact between the tip electrode and the endocardial tissue, the electrode must be firmly anchored relative to the tissue. A number of methods, both passive and active, have been devised for this purpose. In accordance with one known passive fixation technique, a plurality of flexible tines bonded to or molded integrally with the insulative sheath covering the coiled electrical conductors extend rearwardly at an acute angle relative to the longitudinal axis of the lead. Following implantation of the lead, the tines become anchored in the trabecular network of the heart thereby securing the electrode against displacement or dislodgment. In this fashion, the position of the tip electrode is mechanically stabilized, that is, the tip electrode is positively anchored so as to remain in place during the lifetime of the implant. Since the tines can flatten against the lead body and thus reduce its diameter, tined leads are often suitable for introduction through small blood veins. Other known passive fixation techniques include collar electrodes which have one or more conical projections of silicon rubber or other biostable, biocompatible flexible material behind the electrode tip surface. Like the tines, the conical projections become entangled in the trabecular network inside the heart thereby anchoring the tip electrode.

The tip electrode of an active fixation lead may comprise, in accordance with one form thereof, a pointed helix adapted to be screwed into the heart tissue to be stimulated. Rotational torque applied to the connector pin at the proximal end of the lead is transmitted via the flexible, coiled conductor to the helical electrode which is thereby screwed into the heart tissue. In this fashion, the position of the electrode tip is mechanically stabilized. Removal of the screw-in electrode from the endocardium can be effected by counter-rotation of the connector pin. Thus, in a rotatable pin, screw-in type, active fixation lead, the conductor coil is used not only as an electrical conductor coupling for the connector pin and the helix electrode, but also as a tool for extending or retracting the helix electrode relative to the distal tip of the lead during lead fixation by rotating the connector pin.

Occasionally a pacing lead may cause infection. If the infection is refractory to antibiotic therapy, the lead must be surgically removed. In other situations, a patient may receive several leads because of "exit block" or because they have required pacing therapy since childhood. In these situations, it would be ideal if the superfluous leads were easily removed with little risk to the patient. One possibility is to provide a lead that has a uniform diameter and is made of a material that does not "stick" to tissue. In the case of passive leads, the fixation tines at the distal tip are typically encapsulated with fibrotic tissue and are difficult to extract. In fact, leads are sometimes so heavily fixated, they come apart during the extraction process. Fragments are often left behind, which is highly undesirable because it may entail a risk of reinfection and may also obstruct the insertion of a new pacing lead. Active fixation leads are less subject to explantation difficulties because the helix tip electrode typically does not resist unscrewing and removal. Nevertheless, on occasion fibrotic encapsulation makes removal of even an active fixation lead difficult with attendant risk to the patient. Thus, lead designs that facilitate explantation are of great value.

To avoid destruction of a pacing lead during extraction it is possible, for example, to use a tubular "cut-loose" catheter which fits outside and around the pacing lead and which can be advanced towards the tip electrode along the pacing lead. At its forward end the cut-loose catheter is provided with a cutting edge for cutting through the encapsulating fibrotic tissue, thereby releasing the pacing lead and permitting its extraction. Another useful method is to insert an extraction stylet in the central channel or lumen of the pacing lead. At its forward end this stylet has a protruding helix or screw which can be brought into engagement with the conductor coil of the pacing lead near the electrode tip, thereby making a withdrawal of the entire pacing lead possible without the risk of the electrode tip or a longer forward end section of the pacing lead breaking loose from the remaining part thereof.

The above-described methods, however, do not always work and may also expose the patient to certain risks, for example, the risk of causing tamponade.

Another approach to the problem of managing the removal of an implanted cardiac pacing lead is disclosed in U.S. Pat. No. 5,179,962. In that patent, a cardiac lead includes a distal end portion comprising a fixation assembly having fixation members in the form of extendable wire rods. These fixation members are movable between an inactive retracted position wherein they are completely retracted into the fixation assembly, and an active extended position wherein they protrude obliquely backwards from the outer surface of the assembly. The fixation members protrude in a barb-like manner from a region of the outer surface of the fixation assembly which is located a short distance behind an annular endocardium contact surface at the distal end of the assembly. The adjustment of the barb-like fixation members between their inactive and active positions takes place by means of an elongated stylet which is axially displaced within the cardiac lead and fixation assembly. The front or distal end of this stylet is attached to a retainer which is displaced in a piston-like manner within the fixation assembly. The fixation members have their front ends attached to said retainer. The fixation members extend obliquely backwards from the rear end of the retainer and protrude obliquely backwards through openings in a jacket or sleeve which encloses the fixation assembly on the outside thereof. This jacket or sleeve is made of an electrically insulating material. However, this prior art cardiac lead with retractable/extendable fixation members is complex and therefore difficult and expensive to manufacture.

Yet another implantable pacing system lead including a detachably connected tip electrode is disclosed in European patent application No. 041254 published Dec. 9, 1981. The lead disclosed in this application includes a connector having a distal threaded end received by an internally threaded sleeve formed integrally with the tip electrode. The proximal end of the connector has a bore for receiving a coil conductor. The coil conductor is fixed to the wall of the bore by means of a longitudinal pin disposed within the lumen of the conductor. The diameter of the pin is such that the pin forces the coil conductor into secure engagement with the wall of the connector bore. The pin includes at its proximal end a profiled section in the form of a groove for receiving a correspondingly shaped distal end of a removal stylet. Rotation of the removal stylet unscrews the connector from the tip electrode permitting withdrawal of the lead body, leaving behind the implanted tip electrode. The disadvantages of this arrangement is that rotation of the removal stylet relative to the lead body can cause rotation of the tip electrode with consequent tissue damage, risk of infection, and so forth.

SUMMARY OF THE INVENTION

The present invention provides a pacing lead assembly including a lead body that is separable from the tip electrode assembly when the lead fixation means, such as tines, are encapsulated with fibrotic tissue and therefore difficult to extract. Preferably, the lead body is isodiametric and is coated with a "non-sticking" material like Teflon®. In the preferred embodiment, the tip electrode assembly includes a proximal end having a threaded bore while the isodiametric lead body has a screw element received by the threaded bore in the tip electrode assembly. The tip electrode assembly may be separated from the lead body by using a stylet having a specially shaped distal end that can engage a correspondingly shaped socket or channel in the proximal end of the threaded element. Holding the lead body stationary, that is, against rotation, the stylet is rotated in a direction to unscrew the threaded element from the tip electrode assembly thereby disconnecting the lead body therefrom. This leaves the small tip electrode assembly behind in the fibrotic tissue. Since the lead body is isodiametric and is coated with a non-sticking material, the lead may be easily rotated and ultimately extracted by traction. The proximal end of the tip electrode assembly and the distal end of the lead body have complementary interengaging stop surfaces that prevent rotation of the tip electrode assembly during rotation of the special stylet so that rotation of the tip assembly and consequent injury is prevented.

In accordance with one specific exemplary embodiment of the invention, there is provided a body implantable lead assembly adapted to transmit electrical signals between a proximal end portion of the lead assembly and a distal end portion of the lead assembly and to thereby stimulate selected body tissue and/or sense electrical signals therefrom. The lead assembly has a longitudinal axis and comprises a lead body lying along the longitudinal axis, the lead body having a proximal end and a distal end. A rotatable threaded element is carried by the distal end of the lead body. An electrical conductor extends between the proximal end and the distal end of the lead body for transmitting the electrical signals, the conductor having a distal end. A sheath of insulative, biocompatible material encloses the electrical conductor for electrically insulating the electrical conductor from body tissue and body fluids. A tip electrode, disposed at the distal end of the lead body, is electrically connected to the distal end of the electrical conductor, and further has a proximal end including a threaded bore. The rotatable threaded element is screwed into the threaded bore, whereby unscrewing of the rotatable threaded element disconnects the tip electrode from the electrical conductor and disengages the lead body from the tip electrode.

In accordance with another aspect of the invention, the proximal end of the tip electrode and the distal end of the lead body have interengageable surfaces preventing relative rotation between the tip electrode and the lead body during unscrewing of the rotatable threaded element, thereby preventing injury which might result from rotation of an encapsulated tip electrode. The interengageable surfaces preferably comprise complementary, longitudinal surfaces extending radially relative to the longitudinal axis.

In accordance with yet another aspect of the invention, the tip electrode has an active surface including a plurality of concentric ridges coaxial of the longitudinal axis of the lead assembly. Such concentric ridges tend to prevent displacement or microdislodgment of the tip electrode relative to the myocardium. Still further, at least the lead body and the tip electrode of the lead assembly of the present invention are isodiametric thereby facilitating extraction of the lead body once uncoupled from the tip electrode.

In accordance with yet another feature of the present invention, the electric conductor comprises a coiled conductor having a lumen. The rotatable threaded element has a proximal end configured to mate with the distal end of a rotatable stylet insertable into the lumen of the coiled conductor, rotation of the stylet unscrewing the rotatable threaded element.

BRIEF DESCRIPTION OF THE DRAWINGS

Further objects, features and advantages of the invention will become apparent from the Detailed Description of the Preferred Embodiments, below, when read in conjunction with the accompanying drawings, in which:

FIG. 1 is a simplified side view of an endocardial pacing lead assembly in accordance with the present invention, the pacing lead assembly including a tip electrode assembly shown implanted in the myocardium of a heart;

FIG. 2 is a side view of the pacing lead assembly of FIG. 1 showing separation of the lead body of the pacing lead assembly from the tip electrode assembly when the tip electrode assembly has become chronically implanted in the myocardium;

DETAILED OF THE PREFERRED EMBODIMENTS

Figure 3:
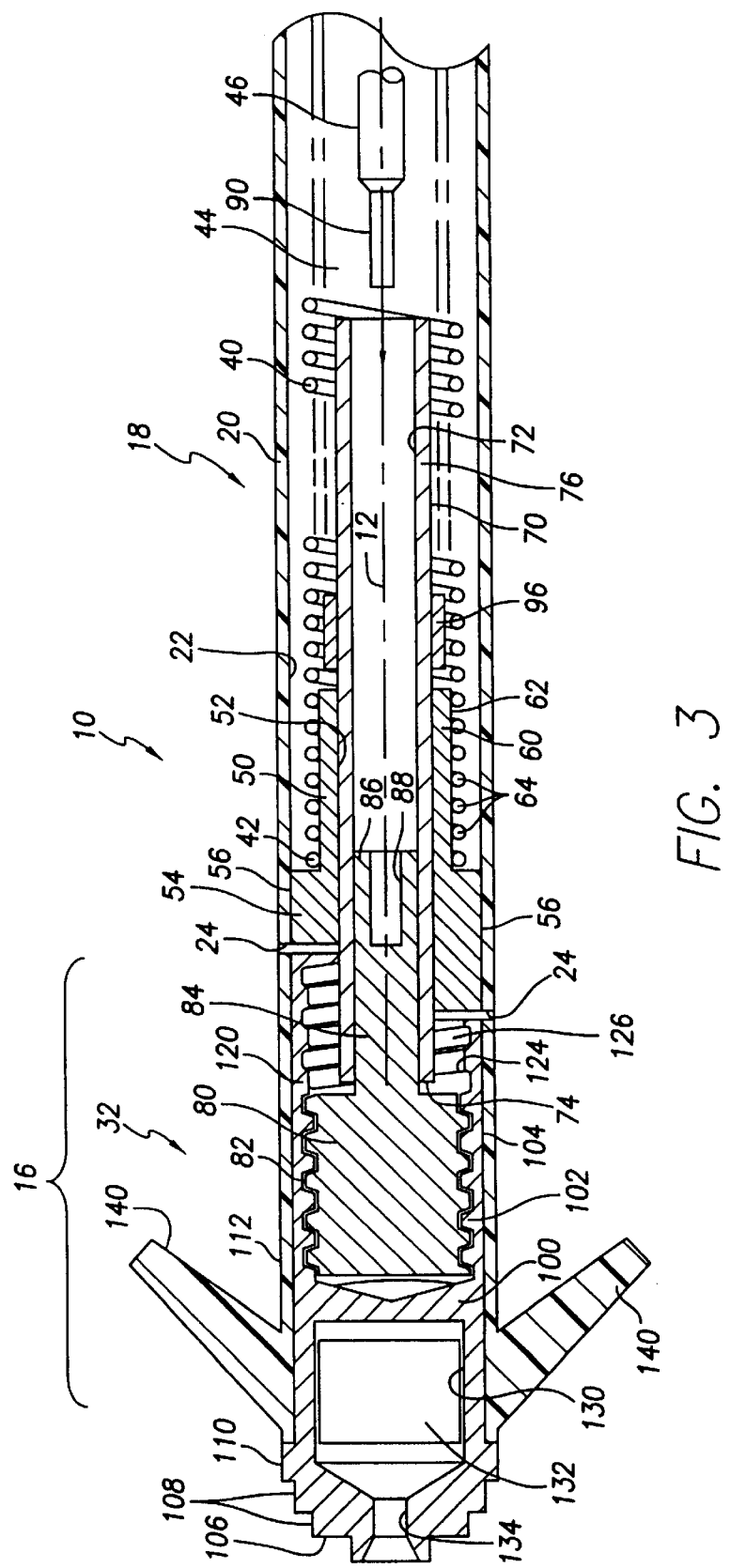
FIG. 3 is a longitudinal cross section view of the distal end portion of the pacing lead assembly of FIG. 1.

The following description presents the preferred embodiments of the invention representing the best modes contemplated for practicing the invention. This description is not to be taken in a limiting sense but is made merely for the purpose of describing the general principles of the invention whose scope is defined by the appended claims. Moreover, the context in which the invention is shown and described herein, that is, specific passive unipolar endocardial implantable pacing and sensing lead, is illustrative only; it will be understood by those skilled in the art that the invention may be used in a wide variety of body implantable tissue stimulating leads, whether passive or active or whether unipolar, bipolar or multipolar.

Referring now to the drawings, there is shown a unipolar, endocardial pacing and sensing lead assembly 10 having a longitudinal axis 12, a proximal end portion 14, a distal end portion 16 and an intermediate portion or lead body 18 connecting the end portions 12 and 14. The lead body 18 is covered by a tubular insulating housing or sheath 20 made of an insulating, biocompatible, biostable elastomeric material such as polyurethane or silicone rubber. The sheath has an interior surface 22 and a distal extremity 24. The proximal end portion 14 of the lead assembly 10 is adapted to be plugged into the socket or receptacle of a pulse generator 26 and for this purpose the elastomeric sheath 20 includes longitudinally space sets of annular ribs 28 for engaging the wall of the receptacle thereby sealing the receptacle against the entry of body fluids. The proximal end portion 14 of the lead assembly 10 further includes an electrical connector pin 30. As is well known, the pin 30 is adapted to engage a corresponding terminal within the receptacle of the pulse generator 26. The distal end portion 16 of the lead assembly 10 comprises a tip electrode assembly 32 for engaging the tissue to be stimulated, for example, the myocardium 34.

The lead body 18 encloses a flexible electrical conductor coil 40 having a proximal end electrically connected to the connector pin 30 and a distal end 42 electrically coupled to the tip electrode assembly 32 in a manner explained below. As is well known in the art, the coil conductor 40 may comprise a multifilar conductor for decreased elongation, increased tensile strength and redundancy to provide continued stimulation and sensing in the event one of the conductor strands breaks. Further, the connector pin 30 on the proximal end portion 14 of the lead assembly is hollow so that in accordance with well known implantation techniques, a stylet may be passed through the hollow connector pin 30 and the central channel or lumen 44 of the conductor coil 40 to enable the implanting physician to maneuver the distal end portion 16 of the lead assembly 10 to position the tip electrode assembly 32 under fluoroscopy to a desired location in the heart. In accordance with the present invention, a special stylet 46 is used to disengage the tip electrode assembly 32 from the lead body 18, as will be explained.

Disposed within the sheath 20 is an electrically conductive sleeve 50 having a bore 52 and a distal end comprising a stepped flange 54. The flange 54 has an outer surface 56 bonded to the interior surface 22 of the sheath 20, adjacent the distal extremity 24 thereof, by means of a silicone medical adhesive or the like so that the sleeve 50 is fixed relative to the sheath 20. The stepped flange 54 defines a pair of coplanar longitudinal surfaces 58 extending radially relative to the axis 12. The sleeve 50 includes a proximal end portion 60 having an outer surface 62 engaged by several windings 64 of the conductive coil 40 at the distal end thereof. The windings 64 are appropriately secured, as by welding, to the outer surface 62 of the proximal end portion 60 of the sleeve 50 to provide a firm joint and good electrical contact.

The conductive sleeve 50 carries within its bore a tubular, electrically conductive driver shaft 70 having an inner wall 72, a distal end 74 projecting from the distal end of the stepped sleeve flange 54, and a proximal end 76 projecting from the proximal end portion 60 of the sleeve 50. The tubular drive shaft 70 is thus supported by the sleeve 50 and rotatable therein.

The distal end of the tubular driver shaft 70 carries an electrically conductive, cylindrical threaded element 80 including an exterior surface having threads 82. The threaded element 80 includes a proximal projection 84 extending into and welded to the inner wall 72 of the tubular drive shaft 70 at the distal end thereof so that the threaded element is rotatable with the shaft 70. The threads 82 (shown schematically in the drawings) may comprise a number 120UNM standard thread, comprising 120 threads per inch. The projection 84 has a proximal extremity 86 defining a shaped socket or channel 88 for receiving and mating with a correspondingly shaped driving end 90 of the special stylet 46. The specific cross section of the socket or channel 88 is not critical so long as the stylet 46 is capable of rotatably driving the threaded element 80; it may simply be in the form of a slot for receiving a blade shaped end of the stylet 46.

Welded to the exterior surface of the proximal end 76 of the tubular shaft 70 is a ring or collar 96 which, in cooperation with the threaded element 80, fixes the longitudinal position of the rotatable, tubular shaft 70 relative to the sleeve 50 while at the same time assuring a good electrically conductive path from the conductor coil 40 to the threaded element 80 via the conductive sleeve 50 and the tubular driver shaft 70.

The tip electrode assembly 32 comprises a tip electrode body 100 for passing electrical pacing stimuli developed by the pulse generator 26 to the heart tissue 34 and/or for transmitting naturally occurring electrical signals from the heart to the pulse generator. The tip electrode body 100 is preferably formed of a biocompatible, conductive material such as stainless steel, MP35N, platinum, platinum-iridium, titanium or an equivalent material.

The tip electrode body 100 comprises a main portion 102 preferably having a generally cylindrical outer surface 104 coaxial of the longitudinal axis 12 and a distal extremity which comprises an active electrode or tip surface 106. The outer cylindrical surface 104 of the main portion 102 of the tip electrode body 100 has a diameter equal to that of the outer surface 56 of the sleeve flange 54 so as to be coextensive therewith.

To reduce polarization voltages, the active tip surface 106 may be roughened or texturized or otherwise made porous and/or microporous and/or can be provided with a coating of such materials as titanium nitride, titanium oxide, iridium oxide, platinum black or carbon. All of these materials are known to increase the true electrical surface area to improve the efficiency of electrical performance by reducing wasteful electrode polarization. The active surface 106 of the tip electrode can be fabricated to include dimples, grooves, or micropores or other indentations or recesses in the tip electrode surface for promotion of tissue in-growth to enhance anchoring the lead tip to the tissue. Such indentations can also be used to carry drugs or medications for delivery to the adjoining tissue.

The active surface 106 of the tip electrode body 100 preferably includes a series of concentric ridges 108 the most proximal one of which (110) has an outer diameter larger than that of the main cylindrical portion 102 of the tip electrode body 100. The main cylindrical portion 102 of the tip electrode body 100 is enveloped in a sheath 112 fabricated of an insulating, biocompatible, biostable elastomeric material such polyurethane or silicone rubber. The sheath 112 has an outer diameter equal to that of the outer diameter of the most proximal ridge 110 as well as the sheath 20 enclosing the lead body 18. Accordingly, as best seen in FIG. 3, the lead assembly of the present invention is isodiametric, that is, it has a uniform or constant diameter along substantially its entire length.

Figure 4:
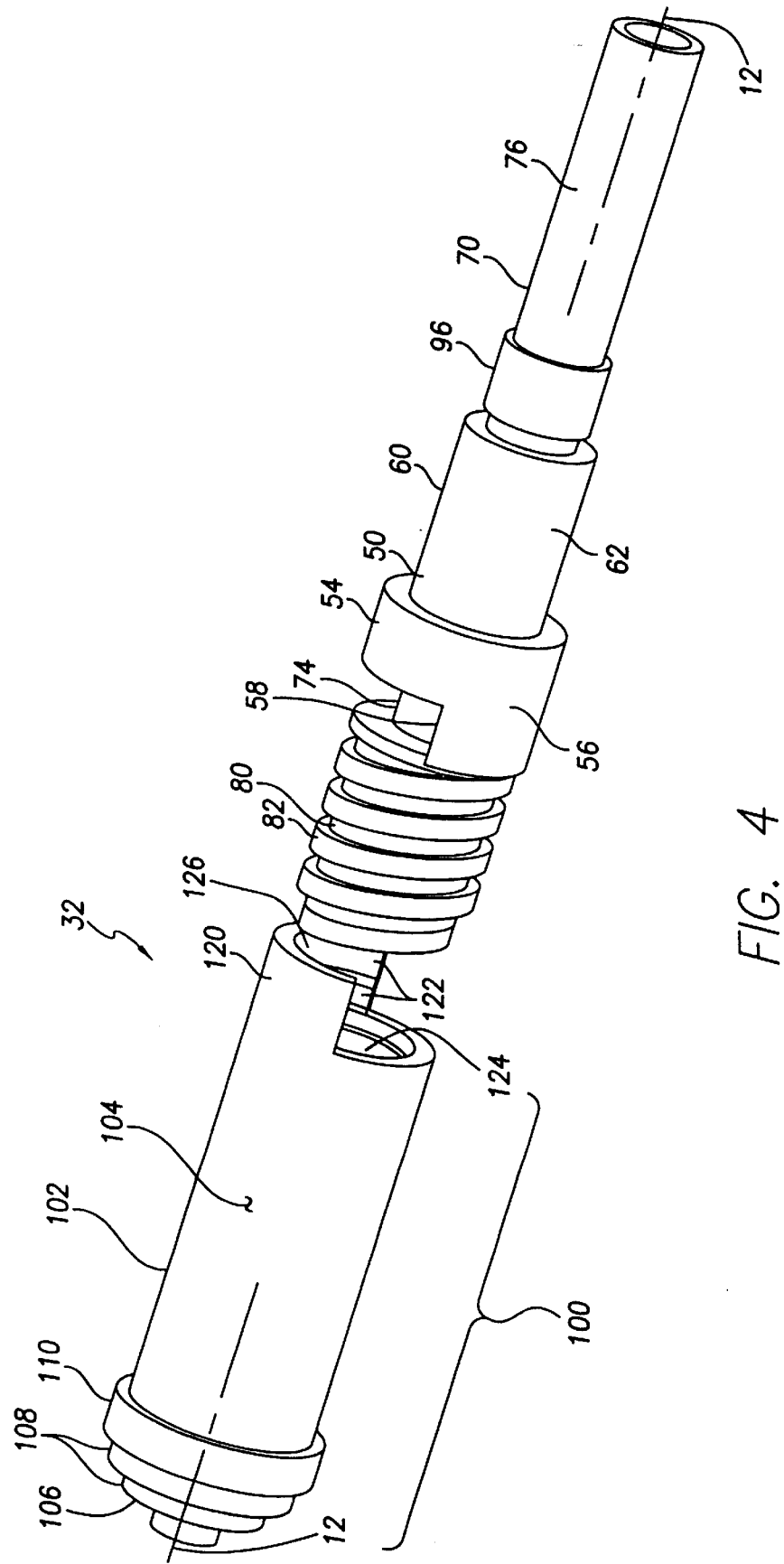
FIG. 4 is a perspective view of the distal end portion of the pacing lead assembly of the invention, with certain elements of the assembly omitted for clarity, after separation of the lead body from a chronically implanted tip electrode assembly.

The tip electrode body 100 has a proximal end 120 that is stepped in a fashion complementary to that of the stepped flange 54 of the sleeve 50. Accordingly, the proximal end 120 of the tip electrode body includes coplanar longitudinal surfaces 122 extending radially relative to the axis 12 and which, as best seen in FIG. 4, are adapted to engage the corresponding surfaces 58 on the flange 54 of the sleeve 50. The proximal end of the tip electrode body 100 further has a bore 124 whose wall is provided with threads 126. The threads 126 on the wall of the bore 124 match the threads 82 on the threaded element 80 which, when screwed into the bore 124, brings into juxtaposition or interengagement the complementary surfaces 58 and 122 on the sleeve flange 54 and the proximal end of the tip electrode body 100, respectively.

The tip electrode body 100 further includes a chamber 130 which houses a plug 132 fabricated of a polymer impregnated with an anti-inflammatory or other therapeutic drug. The chamber 130 communicates with the distal extremity of the active surface 106 of the tip electrode body 100 by means of a channel 134 through which the drug elutes in accordance with principles well known in the art.

The tip electrode sheath 112 includes just behind the active surface 106 of the tip electrode body 100 a plurality of pliant tines 140 projecting rearwardly from the sheath and disposed at an acute angle thereto. Although the tines 140 may comprise separate elements bonded to the sheath 112 by silicone rubber medical adhesive or the like, preferably the tines 140 are molded as part of the sheath 112. The tines 140 serve to anchor the tip electrode body once in place within a chamber of the heart. As is well known, during implantation, as the distal end portion of the lead assembly 10 is advanced within a vein toward the heart, the pliant tines 140 are urged by the wall of the vein to move down into contact with the outer surface of the sheath 112. The angularly oriented tines engage heart tissue so as to urge the tip electrode surface into contact with the myocardium 34 in a direction parallel to the lead axis 12. Although any number of tines 140 may be used, four are preferable.

As is known, forces of the order of 200 grams can be applied to right ventricular and right atrial pacing leads during extraction without compromising blood pressure, the myocardium or lead integrity. However, when a force greater than 400 grams is applied to a right ventricular or right atrial pacing lead, blood pressure, lead integrity and/or the myocardium may be compromised. In the use of the pacing lead of the present invention, an attempt is first made to extract the lead without separating the lead body 18 from the tip electrode assembly 32. If this is unsuccessful, the removable tip technology of the present invention is deployed. The special screwdriver stylet 46 is introduced into the conductor coil lumen and the driving end 90 is inserted into the socket or channel 88 at the proximal end of the threaded element 80. The threaded element 80 is disengaged from the tip electrode assembly 32 by rotating the stylet 46 counterclockwise while holding the proximal end portion 14 of the lead assembly 10 stationary, and then pulling out the lead body 18 leaving the tip electrode assembly 32 and tines 140 in situ.

The stationary lead body 18 prevents rotation of the tip electrode assembly 32 (which rotation could cause injury when the tines tear loose) through the interengaging surfaces 58 and 122 on the sleeve flange 54 and tip electrode body 100. Once the lead body 18 has been disengaged from the tip electrode assembly 32, as seen in FIG. 2, the isodiametric geometry combined with a Teflon® or like coating on the outer surface of the lead body facilitates extraction of the lead body 18.

It should be appreciated that the foregoing description is only illustrative of the invention. Various alternatives and modifications can be devised by those skilled in the art without departing from the spirit of the invention. Accordingly, the present invention is intended to embrace all such alternatives, modifications and variations as fall within the scope of the appended claims.

What is claimed is:

1. A body implantable lead assembly adapted to transmit electrical signals between a proximal end portion of the lead assembly and a distal end portion of the lead assembly and to thereby stimulate selected body tissue and/or sense electrical signals therefrom, the lead assembly having a longitudinal axis and comprising:

a lead body lying along the longitudinal axis, the lead body having a proximal end and a distal end;

a rotatable threaded element carried by the distal end of the lead body;

an electrical conductor extending between the proximal end and the distal end of the lead body for transmitting the electrical signals, the conductor having a distal end;

a sheath of insulative, biocompatible material enclosing the electrical conductor for electrically insulating the electrical conductor from body tissue and body fluids; and a tip electrode disposed at the distal end of the lead body, the tip electrode being electrically connected to the distal end of the electrical conductor, the tip electrode having a proximal end including a threaded bore, the rotatable threaded element being screwed into the threaded bore, wherein unscrewing of the rotatable threaded element disconnects the tip electrode from the electrical conductor and disengages the lead body from the tip electrode.

2. A lead assembly, as defined in claim 1, in which the proximal end of the tip electrode and the distal end of the lead body have interengageable surfaces preventing relative rotation between the tip electrode and the lead body during unscrewing of the rotatable threaded element.

3. A lead assembly, as defined in claim 2, in which the interengageable surfaces comprise complementary, longitudinal surfaces extending radially relative to the longitudinal axis.

4. A lead assembly, as defined in claim 1, in which the tip electrode has an active surface and a chamber for housing a drug-impregnated plug, the tip electrode further including an elution channel providing communication between the cavity and the active surface of the tip electrode.

5. A lead assembly, as defined in claim 1, which includes a plurality of passive fixation tines extending outwardly from the tip electrode.

6. A lead assembly, as defined in claim 1, in which the tip electrode has an active surface including a plurality of concentric ridges for preventing microdislodgment.

7. A lead assembly, as defined in claim 1, in which at least the lead body and tip electrode are isodiametric.

8. A lead assembly, as defined in claim 1, in which:

the electric conductor comprises a coiled conductor having a lumen; and the rotatable threaded element has a proximal end configured to mate with the distal end of a rotatable stylet insertable into the lumen of the coiled conductor, rotation of the stylet unscrewing the rotatable threaded element.

* * * * *